US005583020A

United States Patent [19]

Sullivan

[11] Patent Number: 5,583,020
[45] Date of Patent: Dec. 10, 1996

[54] PERMEABILITY ENHANCERS FOR NEGATIVELY CHARGED POLYNUCLEOTIDES

[75] Inventor: Sean Sullivan, Boulder, Colo.

[73] Assignee: Ribozyme Pharmaceuticals, Inc., Boulder, Colo.

[21] Appl. No.: 155,474

[22] Filed: Nov. 19, 1993

Related U.S. Application Data

[63] Continuation-in-part of Ser. No. 980,982, Nov. 24, 1992, abandoned, and Ser. No. 148,169, Nov. 4, 1993, which is a continuation of Ser. No. 983,326, Nov. 30, 1992.

[51] Int. Cl.$^6$ ............... C12N 15/00; A61K 31/70; C07D 233/16
[52] U.S. Cl. ............ 435/172.3; 514/44; 548/335.1; 560/1; 564/230; 564/384; 564/463; 564/509
[58] Field of Search ............ 514/44; 435/172.3; 536/22.1, 23.1, 24.5; 530/350; 560/1; 564/230, 284, 436, 509

[56] References Cited

U.S. PATENT DOCUMENTS

| 4,394,448 | 7/1983 | Szoka, Jr. et al. . |
| 4,701,521 | 10/1987 | Ryser et al. . |
| 4,847,240 | 7/1989 | Ryser et al. . |

FOREIGN PATENT DOCUMENTS

| 9118012 | 11/1991 | WIPO . |
| 9318759 | 9/1993 | WIPO . |

OTHER PUBLICATIONS

Norrie et al (1982) Analyt. Chem. 127, 276–281.
Wagner et al., "Transferrin–Polycation–DNA Complexes: The Effect of Polycations on the Structure of the Complex and DNA Delivery to Cells," [Abstract] *Proc. Natl. Acad. Sci. USA* 88:4255 (1991).
Cotten et al., "Transferrin–Polycation–Mediated Introduction of DNA into Human Leukemic Cells: Stimulation by Agents that Affect the Survival of Transfected DNA or Modulate Transferrin Receptor Levels," [Abstract] *Proc. Natl. Acad. Sci. USA* 87:4033 (1990).
Zenke et al., "Receptor–Mediated Endocytosis of Transferrin–Polycation Conjugates: An Efficient Way to Introduce DNA into Hematopoietic Cells," [Abstract] *Proc. Natl. Acad. Sci. USA* 87:3655 (1990).
Wagner et al., "Transferrin–Polycation Conjugates as Carriers for DNA Uptake into Cells," [Abstract] *Proc. Natl. Acad. Sci. USA* 87:3410 (1990).
Wu et al., "Receptor–Mediated Gene Delivery in vivo. Partial Correction of Genetic Analbuminemia in Nagase Rats," [Abstract] *J. Biol. Chem.* 266:14388 (1991).
Ryser, Hugues J.-P., "A Membrane Effect of Basic Polymers dependent on Molecular Size," *Nature* 215:934–936 (1967).
Lemaitre et al., "Biological Activities of Oligonucleotides Linked to Poly(L–Lysine)," *Nucleosides & Nucleotides* 6:311–315 (1987).
Ryser, H. J.-P., "Uptake of Protein by Mammalian Cells: An Underdeveloped Area," *Science* 159:390–396 (1968).
Loeffler et al., "Lipopolyamine–Mediated Transfection Allows Gene Expression Studies in Primary Neuronal Cells," *Journal of Neurochemistry* 54:1812–1815 (1990).

*Primary Examiner*—Jacqueline M. Stone
*Assistant Examiner*—Deborah Crouch
*Attorney, Agent, or Firm*—Lyon & Lyon

[57] ABSTRACT

This invention features permeability enhancer molecules, and methods, to increase membrane permeability of negatively charged polymers thereby facilitating cellular uptake of such polymers.

30 Claims, 9 Drawing Sheets

PERMEABILITY ENHANCER ALONE

PERMEABILITY ENHANCER WITH CELL SURFACE RECEPTOR
LIGAND ESTER LINKAGE

AMIDE LINKAGE

*FIG. 1*

A. Small Molecule Ligands
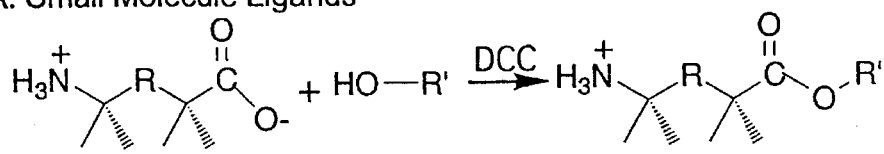
R = a) $(CH_2)_n$ n= 1-10
    b) $(C_6H_6)_n$ n=1-3
    c) a + b
R' = a) carbohydrate
     b) vitamin or vitamin analog
     c) hapten
DCC=dicyclohexylcarbodiimide
B. Proteins, Protein Fragments and Peptides
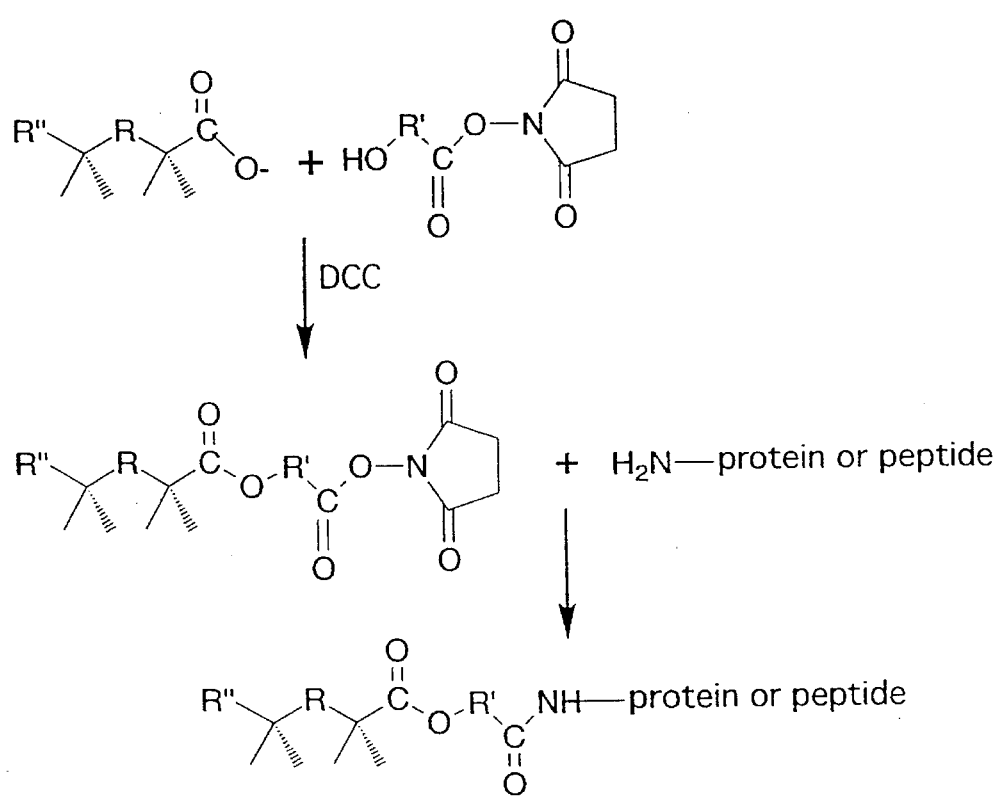
R = $(CH_2)_n$ n=1-10 or $(C_6H_6)_n$ n=1-3
R' = $(CH_2)_n$ n=1-3 or $-CH_2-O-CH_2-$
R" = $CH_3-NH_2^+-$ or $(CH_3)_2-NH^+-$ or $H_2N-\underset{\underset{NH_2^+}{\|}}{C}-NH-$
Fig. 4.

DIMETHYLAMINOBENZYL POLYANHYDRIDE
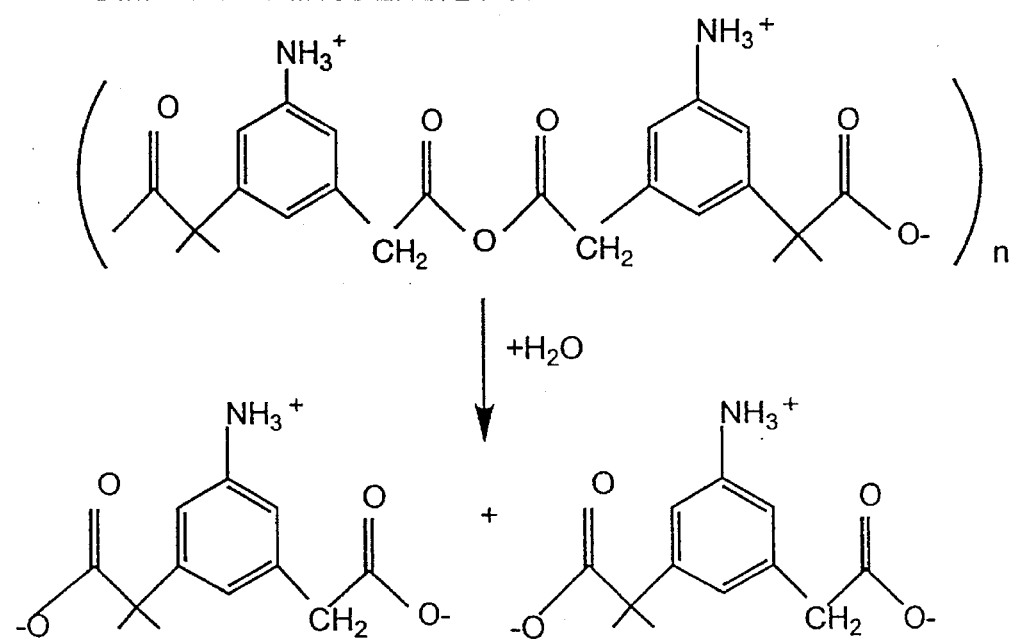
GENERAL POLYANHYDRIDE FORMULA USING :
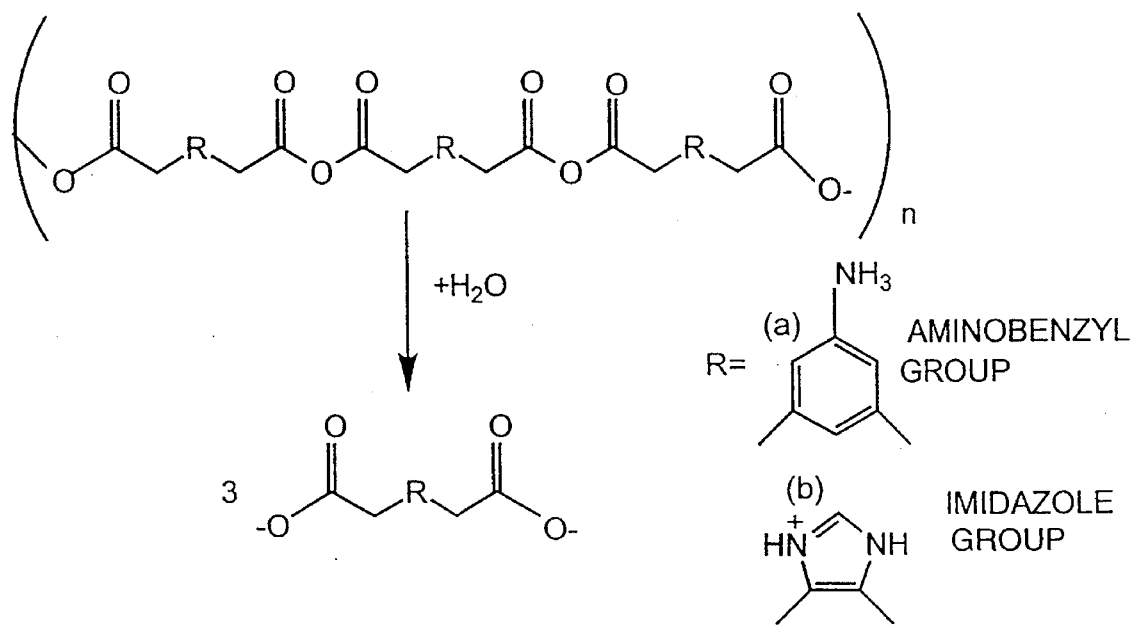
FIG. 6

Primary, Secondary and Tertiary Amines with an Aliphatic Spacer Group

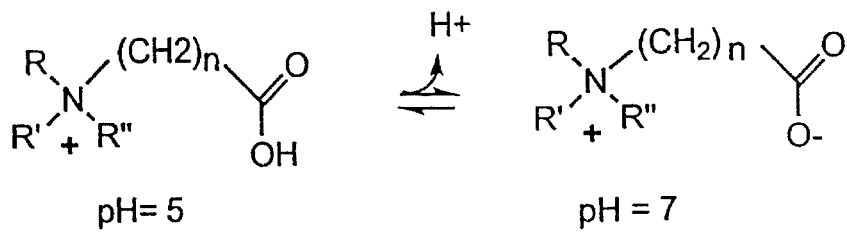

pH= 5            pH = 7 n=3-10
Primary Amine R=R'=R"=H
Secondary Amine R=H; R'=R"=$CH_3$
R=R'=H; R"=$(CH_2)_n$
n=1-8
R=R'=H; R"=

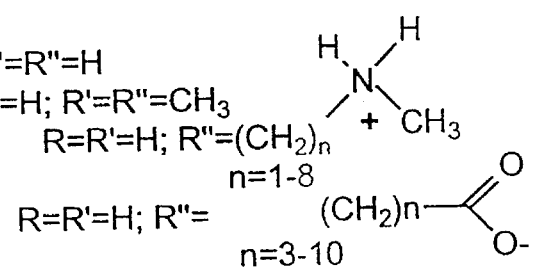

Tertiary Amine R=R'=R"=$CH_3$

Primary, Secondary and Tertiary Amines with
Aromatic and Cyclohexyl Spacer Groups

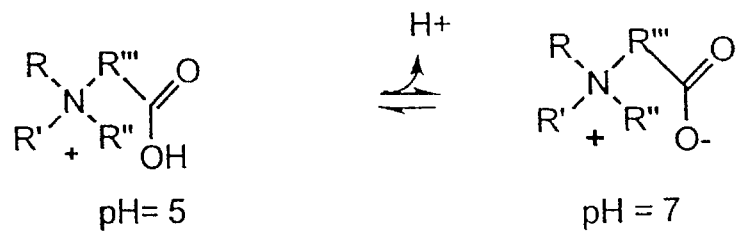

pH= 5            pH = 7 n= 3-10
R'''= $(C_6H_6$-$CH_2)_n$, n=1-3; $(C_6H_{12})_n$, n=1-3
Primary Amine R=R'=R"=H
Secondary Amine R=H; R'=R"=$CH_3$
R=R'=H; R"=$(CH_2)_n$
n=1-8
R=R'=H; R"=

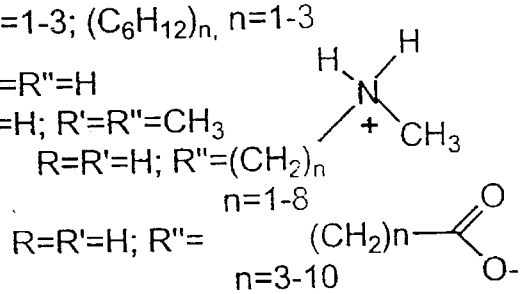

Tertiary Amine R=R'=R"=$CH_3$

*Fig .7*

FIG. 8
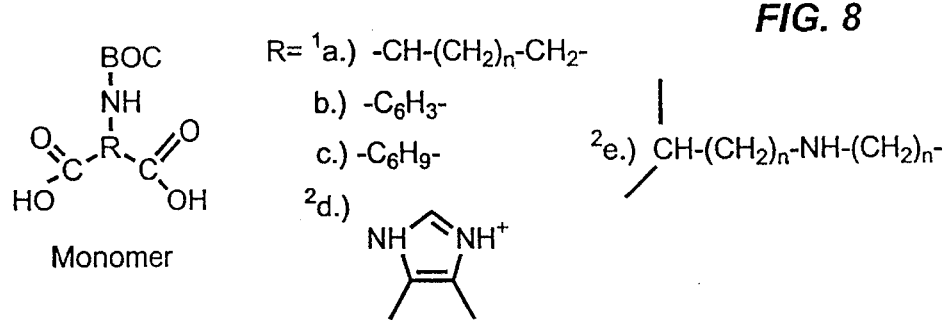
1. n= 2 to 8
2. There is no protected amine with this substituent group
Reaction Scheme
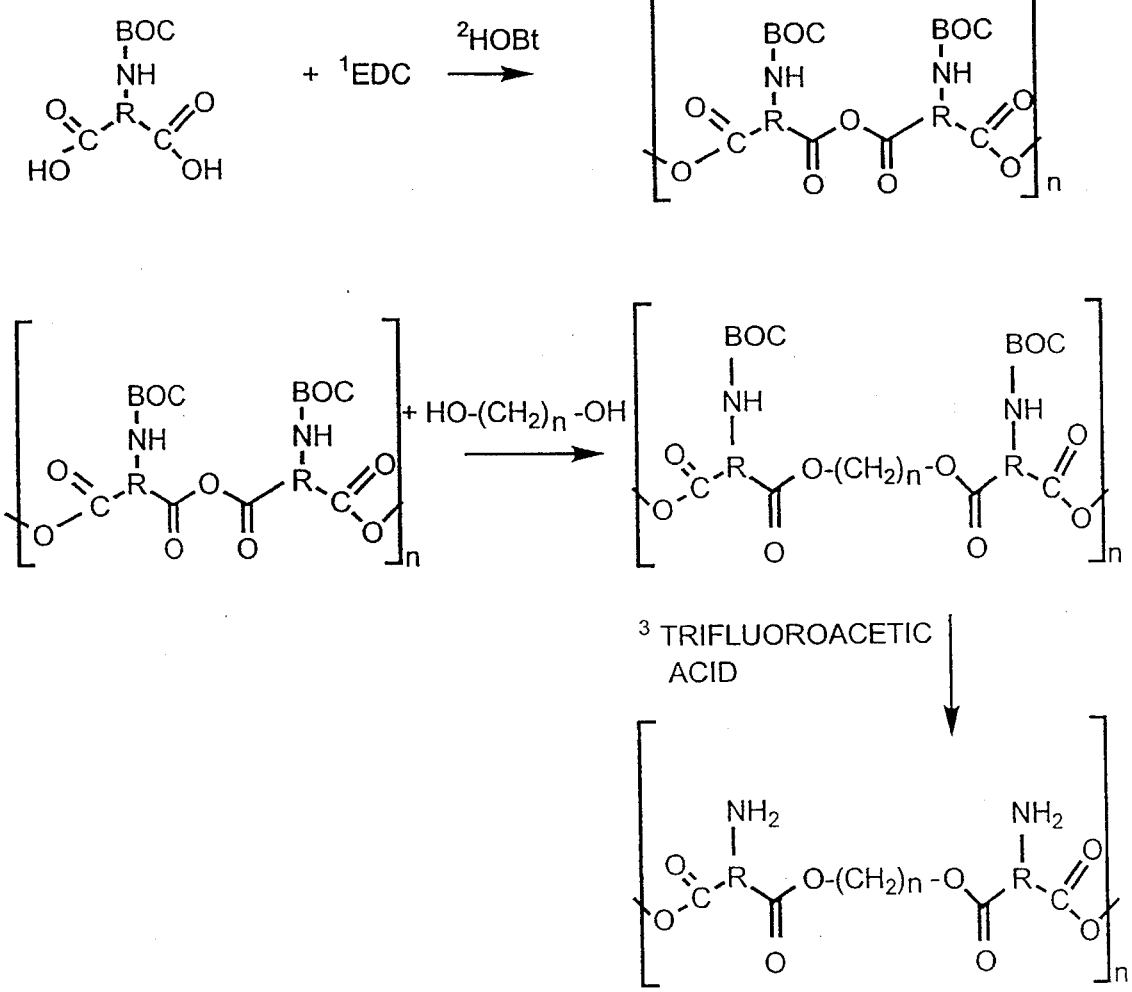
1. EDC= 1-ETHYL-3(3-DIMETHYLAMINOPROPYL)CARBODIIMIDE
2. HOBt=1-HYDROXYBENZOTRIAZOLE-RACEMIZATION AND SIDE REACTION SUPPRESSING REAGENT

PERMEABILITY ENHANCERS FOR NEGATIVELY CHARGED POLYNUCLEOTIDES

RELATED APPLICATION

This application is a continuation-in-part of U.S. application Ser. No. 07/980,982 entitled "pH Dependent Permeability Enhancers For Ionic Therapeutic Polymers," filed Nov. 24, 1992, abandoned and a continuation-in-part of U.S. application Ser. No. 08/148,169, filed Nov. 4, 1993, which is a continuation of U.S. application Ser. No. 07/983,326 entitled "Receptor Targeted Permeability Enhancers", filed Nov. 30, 1992. These prior applications are hereby incorporated by reference herein.

BACKGROUND OF THE INVENTION

This invention relates to compositions and methods which enhance membrane permeability of negatively charged polymers, such as RNA and DNA.

Negatively charged polymers, such as nucleic acid, can be introduced into a cell by a variety of procedures including microinjection, electroporation, and liposome fusion. For example, liposomes made from LIPOFECTIN™ can be used to introduce nucleic acid into eukaryotic cells. Eppstein et al., U.S. Pat. No. 5,208,036 (1993). LIPOFECTIN™ contains an amphipathic molecule having a positively charged choline head group (water soluble) attached to a diacyl glycerol group (water insoluble). Promega (Wisconsin) markets another cationic lipid, TRANSFECTAM™, which can help introduce nucleic acid into a cell.

Wagner et al., 88 *Proc. Nat. Acad. Sci. USA* 4255, 1991, Cotten et al., 87 *Proc. Nat. Acad. Sci. USA* 4033, 1990, Zenke et al., 87 *Proc. Nat. Acad. Sci. USA* 3655, 1990, and Wagner et al., 87 *Proc. Nat. Acad. Sci. USA* 3410, 1990, describe transferrin-polycation conjugates which may include DNA and enhance uptake of that DNA into cells. They also describe receptor-mediated endocytosis of transferrin-polycation conjugates to introduce DNA into hematopoietic cells.

Wu et al., 266 *J. Bio. Chem.* 14338, 1991, describe in vivo receptor-mediated gene delivery in which an asialoglycoprotein-polycation conjugate consisting of asialoorosomucoid is coupled to poly-L-lysine. A soluble DNA complex was formed capable of specifically targeting hepatocytes via asialoglycoprotein receptors present on the cells.

Biospan Corporation WO91/18012 describe cell internalizable covalently bonded conjugates having an "intracellularly cleavable linkage" such as a "disulfide cleavable linkage" or an enzyme labile ester linkage.

SUMMARY OF THE INVENTION

This invention features permeability enhancer molecules, ligand-permeability enhancer molecules, and methods using the featured molecules to increase membrane permeability of negatively charged polymers thereby facilitating cellular uptake of such polymers. Permeability enhancer molecules and ligand-permeability enhancer molecules contain a cationic group which can ion-pair with an anionic group present in a negatively charged polymer. The formation of such ionic pairing reduces the overall charge of the negatively charged polymer and facilitates diffusion of the polymer across a cell membrane.

A permeability enhancer molecule comprises a cationic group covalently linked to weakly acidic anionic group. Preferably, the anionic group has a $pK_a$ between 4.0 and 6.0, and as a result is protonated between pH 5 and 6. As will be recognized by one skilled in the art, anionic groups protonated at a pH between about 5 and 6 will be protonated at a lower pH. The anionic group is preferably greater than 50% unprotonated at pH 7.4, and no greater than 10% unprotonated at pH 5.0 to 6.0. For example, the anionic group may be a carboxylate group with a $pK_a$ between 4.5 and 5.5.

Preferably, the cationic group has little or no positive charge at pH 7.4 (i.e., between 0 and 10% of a positive charge, measured by standard technique), and a greater than 50% positive charge at a pH between 5.0 and 6.0. Examples of such cationic groups include aminobenzyl groups, and imidazoles which have $pK_a$s between 4.0 and 5.0. Groups such as aminobenzyl and imidazoles can optionally be polymerized to form polycationic enhancers. Advantages of polycationic enhancers include allowing the slow release of negatively charged polymers with the moneric units remaining associated with the polymer to facilitate cell entry.

Cationic groups having a non-titratable moiety (e.g. having a moiety which is at least 90% positively charged at both pH 7.4 and 5.0), are less preferred. Enhancers having a non-titratable moiety are also useful in this invention, but require an offset in concentration to trigger dissociation of the enhancer from the ion-paired negatively charged polymer.

The positively charged cationic group can ion-pair with an anionic group present in a negatively charged polymer, such as a phosphate group present in a nucleic acid phosphodiester linkage or a phosphorothioate group present in nucleic acid having a modified phosphodiester linkage. Preferably, the cationic group ion-pairs with a negatively charged polymer such as a polynucleotide or polyaminoacid (e.g. RNA, DNA, and protein). More preferably, the cationic group ion-pairs with RNA having enzymatic activity, such as a ribozyme.

Formation of the ion-pair and protonation of the anion moiety of the permeability enhancer increases the intrinsic hydrophobicity of the negatively charged polymer and facilitates diffusion of the polymer across a cell membrane into the cytoplasm. The cytoplasm of different cells are generally neutral and range in pH from 6.8 to 7.4. In this neutral pH of the cytoplasm, about pH 7.0, the enhancer cationic group is deprotonated neutralizing its positive charge, and the enhancer anionic group is deprotonated providing it with a negative charge. The negative charge of the enhancer may be able to promote the dissociation of the enhancer:polymer complex due to charge repulsion between the negatively charged groups of the enhancer and the polymer. The disassociated negatively charged polymer is trapped within the cellular cytoplasm and unable to diffuse out of the cell.

Thus, in a first aspect a method for enhancing the permeability of a negatively charged polymer is described. The method comprises the step of contacting a negatively charged polymer with a permeability enhancer molecule comprising a cationic group covalently linked to an anionic group. The cationic group carries between 0 and 10% of a positive charge at pH 7.4, and carries a greater than 50% positive charge at a pH between 5.0 and 6.0. The anionic group is greater than 50% unprotonated at pH 7.4 and no greater than 10% unprotonated at pH 5.0 to 6.0.

A protonated cationic group can ion-pair with an anionic group present on a negatively charged polymer to form an enhancer:polymer complex. The enhancer:polymer complex can contain more than one enhancer molecule. Preferably, an enhancer:polymer complex contains enhancers in an amount to ion-pair with at least 50% of the anionic groups of a negatively charged polymer. More preferably, an enhancer:polymer complex contains enhancers in an amount to ion-pair with at least 90% of the anionic groups of a negatively charged polymer. The enhancers of an enhancer:polymer complex can be the same or different. For example, the complex can contain enhancers differing in the cationic group.

The amount of enhancer and negatively charged polymer which should be combined to achieve the desired amount of ionic pairing depends on the environment in which the enhancer and the polymer is mixed, the type of enhancer, and the type of polymer. The degree of ionic pairing can be measured by techniques known in the art. As a general guideline, the enhancer molecule should be provided in an amount of at least two to ten times per negative charge on the polymer molecule.

Preferably, the cationic group is linked to the anionic group through a hydrophobic linker. The use of a hydrophobic linker increases the hydrophobicity of the enhancer. The hydrophobic linker is preferably a hydrocarbon chain. As the linker chain length increases the hydrophobicity of the enhancer also increases. However, as the chain length increases the solubility of the enhancer decreases. The chain length is preferably 4 to 16 carbons, either straight, branched, or cyclic. More preferably, the hydrophobic linker is either a hydrocarbon comprising 3 to 10 carbon atoms, a polyethoxy chain, or an aromatic chain.

In preferred embodiments, the cationic group is a weak base such as an imidazole or aminobenzene, the contacting step is performed at acidic pH so that the enhancer molecule has a net positive charge and ion-pairs via its cationic moiety with an anionic group present in the negatively charged polymer.

In another preferred embodiment, the permeability enhancer molecule is provided within a liposome and co-encapsulated with the negatively charged polymer to be delivered. Liposomes can introduce encapsulated material into a cell by different mechanisms. See, Ostro, *Scientific American* 102, January 1987. For example, the liposome can directly introduce its encapsulated material into the cell cytoplasm by fusing with the cell membrane. Alternatively, the liposome can be compartmentalized into an acidic vacuole (i.e., an endosome) having a pH between 4.5 and 5.5. This low pH allows ion-pairing of the encapsulated enhancers and the negatively charged polymer, which facilitates diffusion of the enhancer:polymer complex out of the liposome, the acidic vacuole, and into the cellular cytoplasm.

In yet another preferred embodiment, the permeability enhancer is provided as a cationic polymer (also referred to herein as "polycationic enhancer"). The enhancer monomers can exist as polymerized molecules containing groups such as a polyester or polyanhydride. These groups have been selected because hydrolysis of these bonds yields carboxyl groups. Negatively charged polymers, such as RNA or DNA can be bound to the cationic groups of the polycationic enhancer. Hydrolysis of the polycationic enhancer leaves the RNA or DNA ion-paired to cationic groups thereby facilitating cellular uptake.

In a related aspect, the invention features a method for enhancing the permeability of a negatively charged polymer molecule using an enhancer molecule having a cationic group carrying at least a 90% positive charge at both pH 7.4 and 5.0. The enhancer also has an anionic group which is greater than 50% unprotonated at pH 7.4, and no greater than 10% unprotonated at pH 5.0 to 6.0.

In another aspect the invention features a targeted permeability enhancer molecule (also referred to herein as "ligand-enhancer") comprising a targeting ligand covalently linked to a cationic group through a biological labile bond. Cleavage of the biologically labile bond results in the formation of an enhancer molecule.

The cationic group of the ligand-enhancer can ion-pair to an anionic group present on a negatively charged polymer to form a ligand-enhancer:polymer complex. Preferably, a ligand-enhancer:polymer complex contains ligand-enhancers in an amount to ion-pair with at least 50% of the anionic groups of a negatively charged polymer. More preferably, a ligand-enhancer:polymer complex contains ligand-enhancers in an amount to ion-pair with at least 90% of the anionic groups of a negatively charged polymer. The ligand-enhancer:polymer complex can contain different types of ligand-enhancers. For example, ligand-enhancers can differ in the structure of the targeting ligand and/or the structure of the enhancers. The ligand-enhancer can be combined with a negatively charged polymer in the same manner as the enhancer is combined with a polymer, as described above.

The targeting ligand of a ligand-enhancer:polymer complex can facilitate transport of the complex into a cell by receptor mediated uptake. For example, the targeting ligand is recognized by a cell receptor which then mediates endocytosis of the ligand-enhancer:polymer complex resulting in the formation of an endosome containing the ligand-enhancer:polymer complex. Preferably, the targeting ligand is either a monoclonal antibody or fragment thereof, a peptide, a carbohydrate, or a vitamin.

The biological labile bond, present in a ligand-enhancer, can be cleaved enzymatically and/or by an acid pH. Preferably, the biological labile bond can be cleaved by an enzyme present in an endosome or by the pH of an endosome. Suitable biological labile bonds produce a weakly acidic anionic group upon enzymatic or acid catalyzed cleavage. The produced anionic group has the properties described above for an enhancer anionic group. Examples of suitable biological labile bonds include an ester bond, a carbamoyl bond, and a peptide bond.

Preferably, the biologically labile bond is covalently linked to the cationic group by a hydrophobic linker. More preferably, the hydrophobic linker is either a hydrocarbon comprising 3 to 10 carbon atoms, a polyethoxy chain, or an aromatic chain.

Specific examples of groups to which a targeting ligand can be attached to form a ligand-enhancer include aminocaprylic acid, p- or m- aminobenzoic acid, aminocyclohexanoic acid, and guanidinocarpylic acid. Polyamines such as polylysine or polyglutamic acid are not appropriate groups because the hydrolysis product does not produce a suitable anionic group (i.e., an enhancer anionic group as described above). Another disadvantage of polyamines is their adjuvant activity in stimulating the immune system.

In related aspects, the invention features methods for using the ligand-enhancer molecules, and enhancer molecules to introduce a negatively charged polymer into a cell.

The molecules and methods of the present invention are particularly advantageous for introducing nucleic acid into a cell. For example, the invention can be used for ribozyme delivery where it is important to intracellularly administer a ribozyme to be active on RNA targets within a cell.

Other features and advantages of the invention will be apparent from the following description of the preferred embodiments thereof, and from the claims.

BRIEF DESCRIPTION OF THE DRAWINGS

FIG. 1 depicts multiple permeability ligand-enhancer molecules bound to an RNA before and after cleavage of the biological labile bond. Biological labile bonds having an ester or an amide linkage are shown.

FIG. 4A depicts a synthetic scheme for attaching small targeting ligands to a permeability enhancer via an ester bond.

FIG. 4B depicts a synthetic pathway for coupling proteins, protein fragments or peptides to a permeability enhancer.

FIG. 6 depicts a polycationic enhancer joined by polyanhydride linkages and the hydrolysis product of the polycationic enhancer.

FIG. 7 depicts enhancers having primary, secondary, and tertiary amines with aliphatic, aromatic, and cyclohexyl linkers.

FIG. 8 depicts a reaction scheme for synthesizing different polycationic enhancers. EDC refers to 1-ethyl-3(3-dimethylaminopropyl)carbodiimide. HOBt refers to 1-hydroxybenzotriazole racemization and side reaction suppressing reagent. Removal of the BOC amino protecting group can achieved using either 20% trifluoroacetic acid in methylene chloride or 4M HCl in dioxane.

DEFINITIONS

Figure 2A:
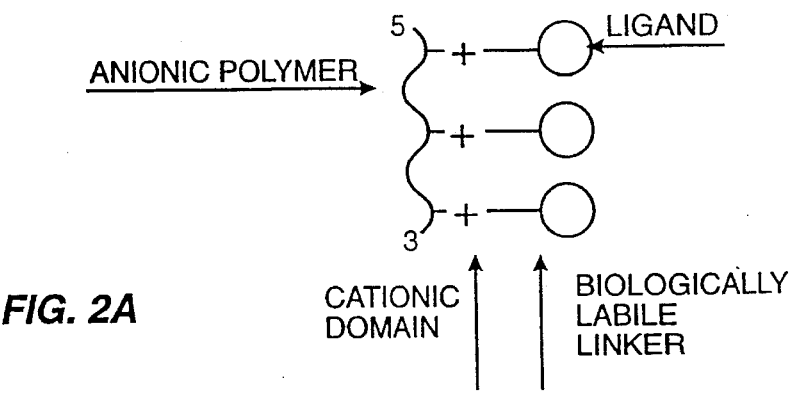
FIG. 2 depicts the recognition of a ligand-enhancer:polymer complex having a biologically labile bond and a hydrophobic linker (2A), the recognition of the ligand-enhancer:polymer by a cell surface receptor (2B), the cellular uptake of the complex into an endocytic vacuole, cleavage of the biological labile bond to form an enhancer:polymer complex, diffusion of the enhancer:polymer complex across a cell membrane, and dissociation of the enhancer from the negatively charged polymer.

A list of definitions used to define some of the terms used in the present disclosure is provided below.

By "receptor mediated uptake" is meant cellular uptake involving the binding of a targeting ligand to a cell surface receptor, preferably occurring by endocytosis triggered by the binding of a targeting ligand to a specific cell surface receptor.

By "targeting ligand" is meant a molecule which binds to a cell surface receptor.

By "ion-pairing" is meant the non-covalent bonding of two oppositely charged molecules.

By "cell surface receptor" is meant a cellular protein associated with the cellular membrane which contains an extracellular domain able to bind a specific ligand. The cellular protein may have attached groups, such as carbohydrate groups.

By "vacuole or endosome" is meant an intracellular compartment surrounded by a membrane having a weakly acidic environment preferably with a pH between 5 and 6.

By "cation" is meant a positively charged molecule.

By "amine" is meant a molecule composed of a nitrogen atom having an $sp^3$ orbital configuration.

By "endocytosis" is meant a cellular process by which cells engulf and internalize extracellular material.

By "antibodies" is meant proteins secreted by immune cells able to specifically bind to an antigen, such as a sequence specific domain on another protein or a small molecule (hapten). The intact antibody is composed of two 50 Kdalton polypeptide chains (heavy chains) and two 25 Kdalton polypeptide chains (light chains) attached by disulfide linkages.

By "Fab" is meant an active fragment of an antibody retaining the binding specificity of the antibody. It is composed of one light chain and half of one heavy chain linked by disulfide linkages. These fragments can exist as a single complex yielding a monovalent binding fragment or multiple fragments.

By "hapten" is meant a small molecule which can bind to an antigen binding site of an antibody, but which cannot induce an immune response.

By "transferrin" is meant an iron transporting protein.

By "adhesive glycoproteins" is meant proteins which bind to cells or other matrix molecules which help cells attach either to each other or to extracellular matrices.

By "growth factors" is meant small molecules or proteins which bind to a cell surface receptor and stimulate cells to divide.

By "vitamin" is meant a small molecule, such as riboflavin, nicotinamide, biotin, thiamine, lipoic acid, retinal, pyridoxal, folate, pantothenic acid, cyanocobalamin, aminopterin, and their respective analogs, which bind to a specific protein and participate directly in enzyme catalysis.

By "major histocompatibility antigen" is meant a family of cell surface glycoproteins which allows the immune system to distinguish self from non-self or stimulates the immune system.

By "cell surface markers" is meant a glycoprotein expressed on the cell surface of an immune cell which distinguishes different stages of immune cell differentiation, (e.g., stem cell versus mature cell) as well as the different types of mature immune cells (e.g., CD4 for T-helper cells, and CD8 for T-suppressor cells).

By "interleukins" is meant proteins secreted by one type of immune cell which upon binding to a cell surface receptor stimulates or suppresses an immune function.

By "complex carbohydrate" is meant a molecule composed of two or more monosaccharides with or without sialic acid or neuraminic acid, and able to bind to an extracellular protein.

By "integrin" is meant a family of cell surface receptors which includes receptors for adhesion to extracellular matrix proteins, as well as receptors involved in various aspects of leukocyte adhesion.

By "small" in relation to a molecule which can act as a targeting ligand is meant a molecule having a molecular weight less than or equal to 1,500 kDaltons.

DESCRIPTION OF THE PREFERRED EMBODIMENTS

Figure 2B:
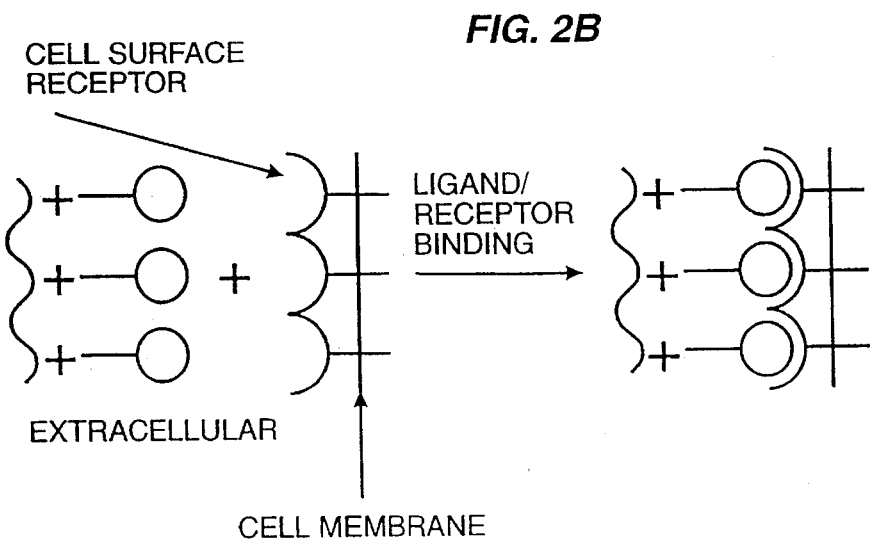
Figure 2C:
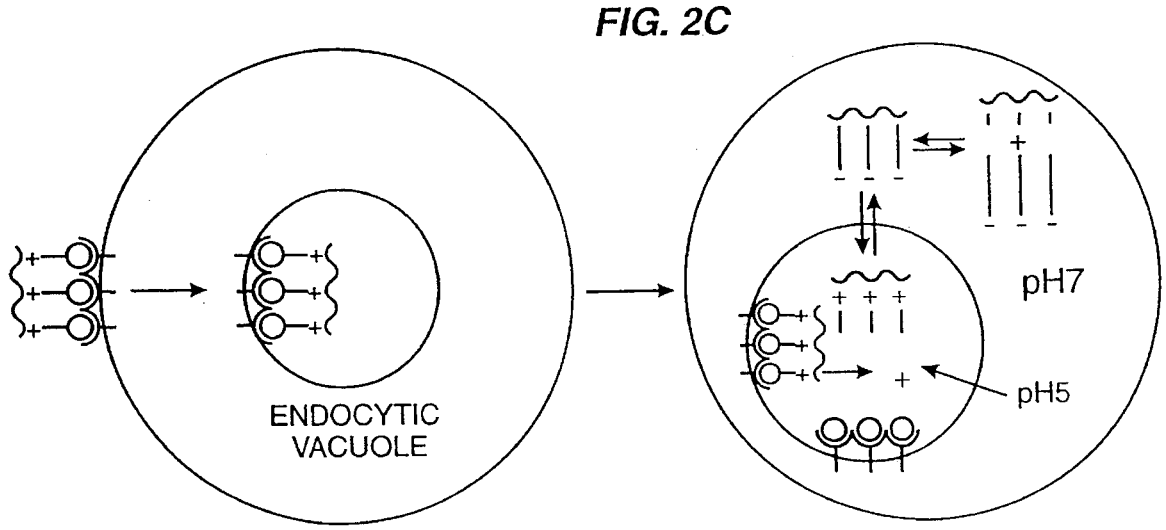

Enhancer and ligand-enhancer molecules described herein can be used to facilitate transport of negatively charged polymers into a cell. FIGS. 1 and 2 show an example of multiple ligand-enhancers bound to an RNA molecule forming a ligand-enhancer:RNA complex, and a mechanism through which RNA is transported into the cytoplasm of a cell.

FIG. 1 shows an example of multiple ligand-enhancers bound to an RNA molecule before and after cleavage of the biological labile group. The cationic group of the enhancer is denoted by a positive charge. The enhancer contains a hydrophobic linker. Two different biological labile bonds are shown in FIG. 1; (1) an amide linkage and (2) an ester linkage.

FIG. 2 illustrates the recognition of a ligand-enhancer:RNA complex by cell surface receptors triggering receptor mediated uptake into an endosome. Inside the endosome the biological labile bond is cleaved producing an enhancer-:RNA complex containing a weakly acidic anionic group. The acidic environment of the endosome results in protonation of the anionic group increasing the intrinsic hydrophobicity of the enhancer:RNA complex by neutralizing the negative charge of the enhancer anionic group, thereby facilitating diffusion of the complex across the endosome membrane into the cytoplasm. In the neutral pH of the cytoplasm, about pH 7.0, the enhancer anionic group is deprotonated thereby acquiring a negative charge, and the enhancer cationic group is protonated thereby neutralizing its positive charge. As a result, the enhancer acquires a net negative charge. The negative charge of the enhancer can aid in the dissociation of the enhancer:RNA complex. Additionally, because the enhancer amino group ion-pairs with the RNA phosphate, there is no covalent bond. The offset of concentrations between the endosome and the cytoplasm (i.e., dilution of the enhancer:polymer complex in the cytoplasm) drives the equilibrium towards dissociation of the amine from the phosphate yielding an unmodified RNA molecule in the cytoplasm. The free RNA cannot diffuse back into the endosome nor can it diffuse out of the cell. The negative charge of the dissociated enhancer can facilitate excretion of the enhancer by the cell.

Enhancers:

The featured enhancer molecules can be used to introduce a negatively charged polymer into a cell. Enhancers should be chosen, or designed, to be readily degraded or excreted by a cell and not to exhibit detergent-like properties upon cellular accumulation. Such enhancers have a decreased cellular toxicity.

Preferably an enhancer has the structure of formula (I):

A—L—C        I

Wherein "A" is a weakly acidic anionic group. Preferably, the anionic group has a $pK_a$ between 4.0 and 6.0. The anionic group should be greater than 50% unprotonated at pH 7.4 and no greater than 10% unprotonated at pH 5.0 to 6.0. For example, the anionic group may be a carboxylate group with a $pK_a$ between 4.5 and 5.5.

Wherein "L" is an optional hydrophobic linker. Preferably, "L" is a hydrocarbon chain of 4 to 16 carbons either straight, branched, or cyclic, comprising one or more alkyl, alkenyl or alkene moiety. More preferably, the hydrocarbon chain has the structure $(CH_2)_n$ (n=1–10, preferably 3–8), $(C_6H_6)_{n'}$ (n'=1–3), $C_6H_3$, $C_6H_9$, a polyethoxy chain, or a combination of these groups.

Wherein "C" is a cationic group having either little or no positive charge at pH 7.4 and a greater than 50% positive charge at a pH between 5.0 and 6.0, or having a non-titratable moiety. Preferably, the cationic group comprises an amine (primary, secondary or tertiary amine, see structures II–IV below) substituted aryl group, an imidazole group, a guanidinium group, or has the structure of formula (II):

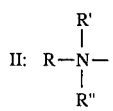

Wherein R, R', R" are independently selected to be either H, $CH_3$, or molecules having structures:

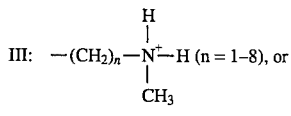

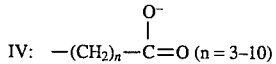

Preferably, the cationic group has one, or less than one, molecule having the structure III or IV. More preferably, the cationic group has no molecules of structure III or IV.

Enhancers have numerous uses including the topical delivery of an DNA or RNA molecule. For example, the stratum corneum of the skin is weakly acidic. An enhancer-:polymer complex applied to the skin would have its anionic group protonated and, thus, no net charge. The charge neutralization of the complex would increase its hydrophobicity and facilitate diffusion of the polymer across a cell membrane. Other sites of topical delivery include the eye (for penetration into the epidermal layer of the cornea), the vaginal epidermal tissue or other mucoid tissues, or to the synovium via intracriticular administration.

Enhancer molecules of the present invention can be used to deliver a negatively charged polymer by co-packaging the polymer and the enhancer into a drug delivery vehicle, such as a liposome. The liposome can be taken up by a cell by endocytosis into an endosome. The enhancer molecule facilitates diffusion of the negatively charged polymer out of the liposome, across the endosome membrane, and into the cellular cytoplasm where it dissociates from the enhancer molecule.

Enhancer molecules can be packaged by liposomes using standard techniques. For example, complex 500 µg of ribozyme with 15 µmol of aminocaprylic acid in 50 µl of water for 0.5 hours. Dilute the solution to 200 µl with 0.3M sucrose. Add the solution to a 10 µmole film of lipid and vortex the lipid into suspension. Freeze and thaw three times and extrude the suspension through a 0.2 µm polycarbonate filter using a miniextruder. Separate the untrapped ribozyme by gel filtration using either a Sepharose CL-4B or Biogen A5M column equilibrated with phosphate buffered saline, pH 7.4. Pool the void peak containing the liposomes.

Enhancer compounds useful in this invention are generally described above. Additional examples of such enhancers are now provided. These examples are not limiting in this invention.

Figure 3:
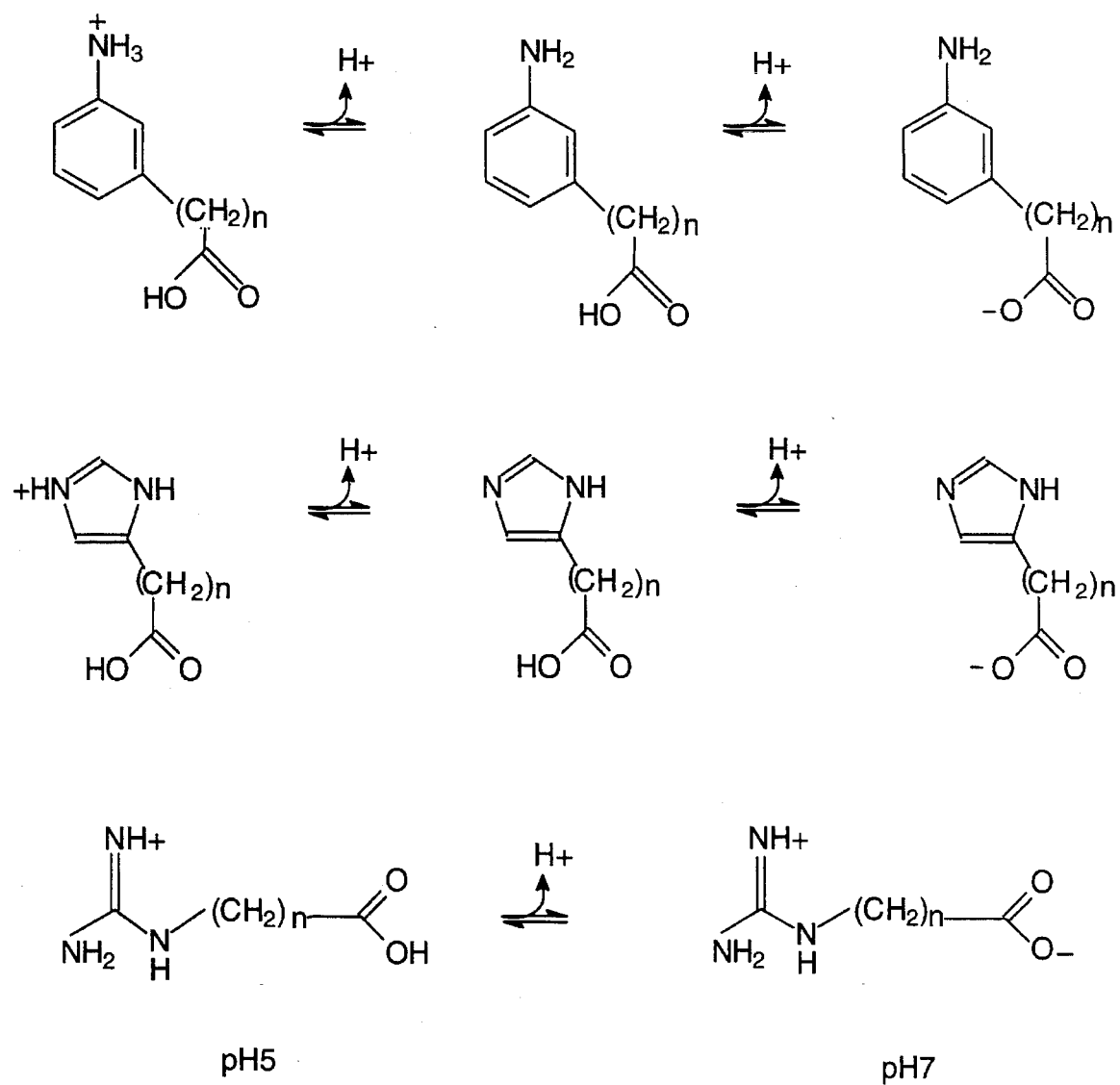
FIG. 3 depicts the equilibrium of various enhancers useful in this invention (n=0–10 inclusive, preferably 3–8).

FIG. 3 depicts the general formula for aminobenzoic acids, imidazoles and guanidinium-based enhancer elements of this invention. In general, the aminobenzoic acid includes an amino group and a carboxylic group. The carboxylic group may be attached to the benzene ring via a hydrophobic linker which is preferably an alkyl, alkenyl or alkene moiety. The benzene ring may be further substituted with other groups so long as the charge requirements (e.g., anionic group $pK_a$, cationic group $pK_a$, and net positive and negative charges) described above are met. Similarly, the guanidinium-based molecule and imidazole-based molecule may have a hydrophobic linker between the carboxylic acid group and the positively charged end, and may also include substituents so long as the charge requirements noted above are met.

Figure 5:
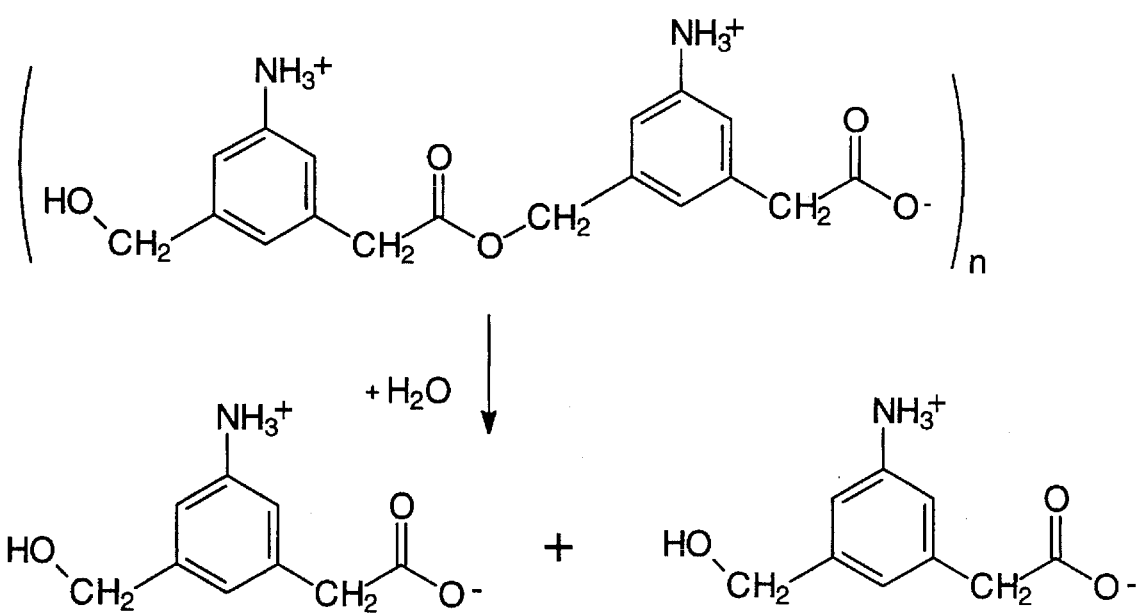
FIG. 5 depicts a polycationic enhancer joined by polyester linkages and the hydrolysis product of the polycationic enhancer.

FIGS. 5 and 6, depicts examples of polycationic enhancer enhancers containing polyester or polyanhydride linkages. "N" represents the number of subunits and can be up to many hundreds or thousands, but preferably is between 100–500. Both the ester and the anhydride polycationic enhancer have labile bonds which spontaneously hydrolyze in aqueous environments. Hydrolysis of the polyesterified molecule yields monomers having a carboxyl group and an alcohol. Hydrolysis of the polyanhydride yields dicarboxylic acid monomers. The polyanhydride and polyester molecules can be stabilized in a dry form, e.g., as lyophilized powders.

Preferably, the negatively charged polymer is ion-paired to an enhancer and stored as a dried powder. This can be achieved by ion-pairing at a pH where the anionic groups are protonated. For example, at a pH where anionic amino groups are protonated (pH 4 to 5 for anilines, pH 5 to 6 for imidazoles, and pH 7 for guanidinium derivatives). The enhancer:polymer complex can be hydrated and administered to a patient.

Polycationic enhancers can be administered in a variety of ways such as topical applications, including skin and genital administration. Polycationic enhancers are especially useful for ocular administration. In this regard, the polycationic enhancer can be used at a concentration wherein the cationic groups of the cationic enhancer polymer exceed the anionic groups of the negatively charged polymer. The excess cationic groups which are not ion-paired serve to adhere the complex to the cornea via a cationic interaction. The aqueous environment of the eye hydrolyses the linked monomers of the polycationic enhancer producing enhancer monomers, having titratable carboxyl groups, ion-paired to the negatively charged polymer. Protonation of the carboxyl group increases the hydrophobicity of the enhancer:polymer complex thereby allowing the enhance:polymer complex to diffuse across the plasma membrane of the corneal epithelial cells and into the cytoplasm. Protonation of the carboxyl group can be achieved by adding a weakly acidic buffered solution to the eye. Alternatively, the hydrolysis may produce a partial breakdown product which can be endocytosed. The acidic environment of the endosome (pH 5–6) will protonate (or neutralize) the carboxyl group allowing the complexed polymer to diffuse across the membrane and into the cytoplasm.

FIG. 7, depicts enhancers having primary, secondary, and tertiary amines with aliphatic, aromatic, and cyclohexyl linkers. Specific examples include primary amines, such as amino acetic acid, piperidinic acid, amino butyric acid, amino caproic acid, amino caprylic acid, 7-amino enanthic acid, and 11-amino undecunoic acid; tertiary amines, such as dimethylamino acetic acid; secondary amines, such as N-dimethylanthranilic acid; aromatic secondary amines, such as aminomethylbenzoic acid, and aminophenylsuccinic acid; and guanidinium-containing molecules, such as guanidino acetic acid, guanidino propionic acid, guanidino butyric acid, guanidino pentanoic acid, guanidino caproic acid, guanidino enanthic acid, guanidino caprylic acid, guanidino pelargonic acid, guanidino lauric acid, guanidino myristic acid, guanidino palmitic acid, and guanidino stearic acid.

Polyesters can be prepared using standard polyester synthesis by bulk polycondensation techniques. (For example, see Asano, et al., *J. Controlled Release* 9:111 (1989)). FIG. 8, depicts a reaction scheme which can be used to synthesize polycationic enhancers.

Ligand-Enhancers

As described above, ligand-enhancer comprise a targeting ligand attached through a biologically labile bond to a cationic group, and cleavage of the biologically labile bond produces an enhancer molecule. The resulting enhancer molecule is as described above. The targeting ligand is a group recognized by a cell receptor. Examples of cell receptor which can be targeted include the insulin receptors, IL-2 receptors, transferrin receptors, EGF and Fc receptors), and viral receptors.

Preferably, a ligand-enhancer has the structure of formula (V):

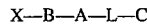   V

Wherein "X" is a targeting ligand. Preferably, X is either a monoclonal antibody or fragment thereof, a peptide, a carbohydrate, or a vitamin.

Wherein "B" is a biological labile bond. Preferably "B" is either an ester bond, a carbamoyl bond, or a peptide bond.

Wherein "A" is an anionic group, as described above for an enhancer, formed by hydrolysis of the biological labile bond.

Wherein "L" and "C" are as described above for an enhancer.

Examples of targeting ligands include a monoclonal antibody (intact IgG, [Fab]$_2$ or Fab) raised against a cell surface antigen (e.g., common to a single cell type which upon binding triggers endocytosis); transferrin; major histocompatibility antigens (class I or II); cytokines; growth factors (e.g., Epidermal Growth Factor (EGF)); cancer specific antigens; interleukins (e.g., IL-1, IL-2, IL-4, IL-6); antibodies to cell surface receptors including intact IgG, IgM, IgA, Fab fragments and Fc; beta-2-microglobulin; fibronectin fragments;laminin fragments; I-CAM; N-CAM; L-CAM; LFA-1; CD4; CD8; CD45; viral attachment proteins such as gp120 (HIV), gB or gD or gC (HSV), HA (influenza, mumps, measles); peptides, such as fibronectin-derived R—G—D); and peptides derived from these proteins which exhibit similar cell surface binding properties as the intact protein.

In addition, a simple or complex carbohydrate (e.g., viral glycoprotein) able to bind to a cell surface receptor, or a vitamin which enables cell entry through a vitamin transporter can be used as a targeting ligand. Examples of useful vitamins recognized by a vitamin transporter include 7-dehydrocholesterol, retinal, lipoic acid, tetrahydrofolic acid, biotin, pyridoxal, niacin, riboflavin, thiamine and respective analogs.

Examples of useful carbohydrates which aid in binding to a cell surface receptor include galactose-3-sulfate, N-acetylneuraminic acid (sialic acid), muramic acid, d-glucuronic acid-(1→3)N-acetyl-D-glucosamine (β-GlcUA-(1→3)-β-GlcNAc), D-glucuronic acid-(1→3)-N-acetyl-D-galactosamine (β-GlcUA-(1→3)-β-GalNAc), and L-iduronic acid-(1→3)-N-acetyl-D-galactosamine-4-sulfate (α-L-iduronic acid-(1→3)-GalNAc-4-sulfate).

Examples of amino acids and peptides which can be used as targeting ligands include single amino acids which utilize the amino acid transporter. The amino acid transporter is divided into three classes: (1) arginine-glycine-serine (binds to fibronectin receptor); (2) muramyl di- and tri-peptide (for targeting to immune cells); (3) lysine-lysine-arginine-lysine (nuclear targeting peptide).

FIG. 4 depicts a targeting ligand covalently attached to a hydrocarbon chain by an ester linkage. The targeting ligand, shown as R', is at one end of the molecule and an amine group is at the opposite end. The amine carries a positive charge (cation) which ion-pairs an anionic group of a negatively charged polymer. Upon incubation with the cell the targeting ligand binds to a cell surface receptor. The presence of multiple targeting ligands in a ligand-enhancer-:polymer complex increasing the binding affinity of the complex. Furthermore, the multiple occupancy of the receptors by the ligands of a ligand-enhancer:polymer complex causes patching of the receptors triggering endocytosis.

As discussed above, endocytosis is a process by which the plasma membrane pinches off and forms a vacuole (endosome). The internal pH of the endosome is acidic. Also, present in the endosome are esterases. The endosome acid and/or esterases catalyze hydrolysis of the biological labile bond present in the ligand-enhancer:polymer producing a ligand and an enhancer:polymer complex.

FIG. 4A depicts a synthetic scheme for attaching a targeting ligand to an enhancer molecule. The scheme is suitable for low molecular weight targeting ligands (vitamins, carbohydrates and amino acids).

Attaching a ligand to an enhancer having a primary amine as the cationic moiety requires a protecting group, such as t-butyloxycarbonyl(BOC) or 9-fluorenylmethyloxycarbonyl (FMOC), to prevent the enhancer from reacting with itself during the dicyclocarbodiamide (DCC) reaction. The protecting group can be removed using a weak acid. A protecting group is not necessary if the enhancer has a secondary amine, a tertiary amine, or a guanidinium group.

The following example uses a primary amine as the cationic moiety of the permeability enhancer:

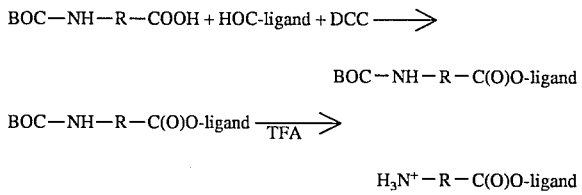

The primary amine is shown as being protected by BOC. TFA refers to trifluoroacetic acid.

FIG. 4B depicts a synthetic scheme for attaching targeting ligands such as intact proteins, protein subunits, proteolytic fragments, peptides or amino acids to a permeability enhancer. As with the low molecular weight targeting ligands, the amino group needs to be protected until after coupling. An alternative is to use secondary or tertiary amines, or guanidinium groups.

Figure 9:
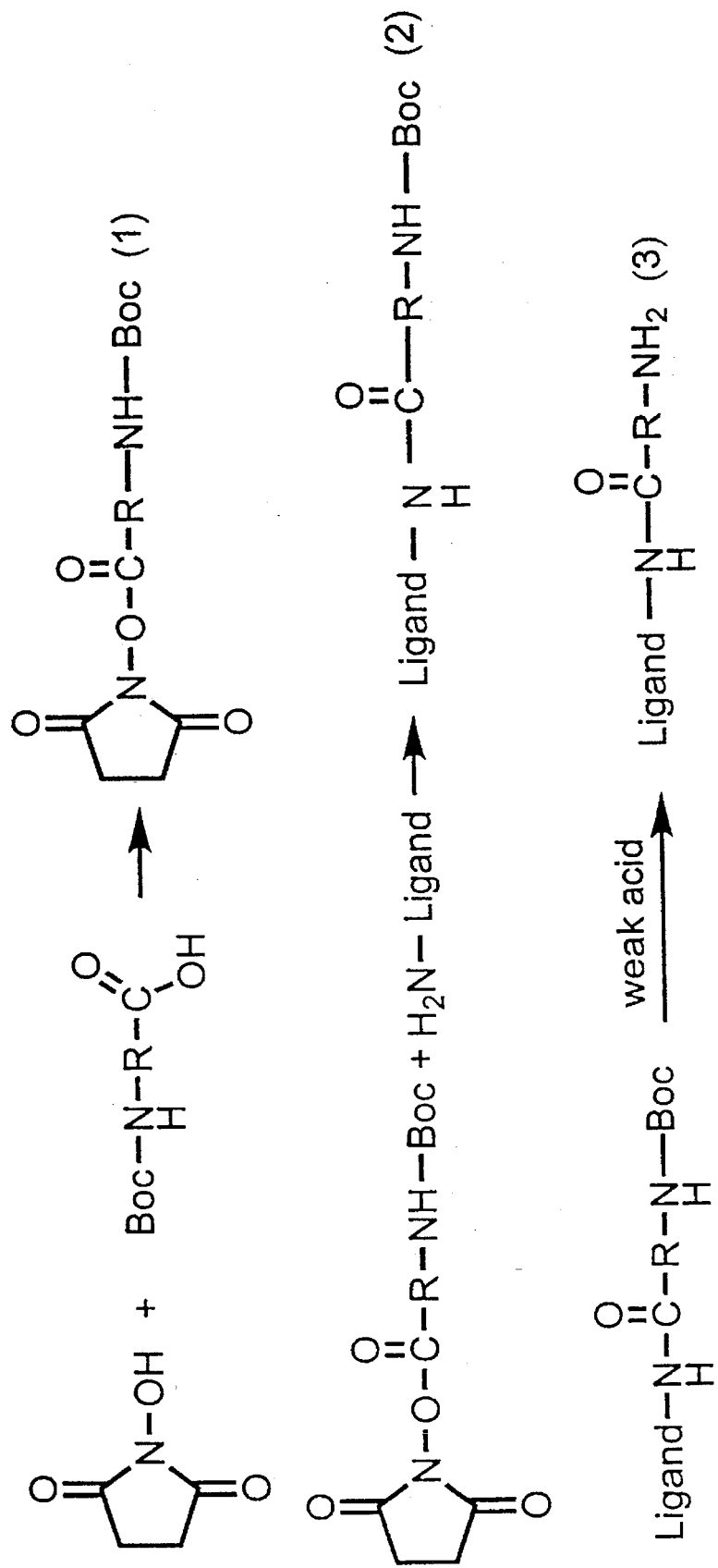
FIG. 9 depicts the derivatization of primary amine containing ligand with permeability enhancer.

An alternative way to couple a permeability enhancer to a ligand is through an amide bond. FIG. 9 shows a reaction scheme for coupling a ligand to a permeability enhancer using an amide linkage. In the first reaction, the N-hydroxysuccinimide activated ester of the permeability enhancer is prepared according to Lapidot et al., *Journal of Lipid Research* 8:142 (1967). The permeability enhancer containing a BOC protected primary amine is substituted for the lauric acid in the Lapidot protocol. Formation of the ligand coupled to the permeability enhancer is prepared according to Sullian and Huang, *Biochem. Biophys. Acta* 812:116 (1985). The BOC group is removed using standard procedures, such as using TFA.

Methods

Enhancer molecules and ligand-enhancer molecules can be used to administer negatively charged polymers which act as pharmaceutical agents. Pharmaceutical agents prevent, inhibit the occurrence, or treat (alleviate a symptom to some extent, preferably all of the symptoms) of a disease state.

Generally, these molecules are used in solution with the negatively charged polymer to be administered (e.g., RNA, DNA or protein) and introduced by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described above, preferably in combination with the negatively charged polymer to be delivered. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration into a multicellular organism such as a mammal, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used. Id.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

The examples provided herein illustrate different aspects and embodiments of the present invention. These examples are not intended in any way to limit the disclosed invention.

EXAMPLE 1

Diffusion Across A Liposome Membrane

This example illustrates the ability of different enhancers to facilitate the diffusion of a ribozyme across a liposome membrane. The ribozyme was a 36 mer containing five 2'-O-methyl riboses at the 5' end and the 3' end. The ratio of permeability enhancer molecules per mole of phosphate was about 20:1.

Specifically, twenty μg of $^{32}$P radiolabeled ribozyme ($1.68\times10^{-9}$ moles) was incubated with $1.2\times10^{-6}$ moles of permeability enhancer in 50 μl of water to give a pH of about 4. Incubation was carried out at 25° C. for 15 minutes. After the incubation, $1\times10^{-11}$ moles of dioleoylphosphatidylcholine liposomes was added to the 50 μl solution. The solution was diluted to 100 μl with 20 mM HEPES (pH 7.4) and centrifuged in a microfuge for 5 minutes to pellet the liposomes. The supernatant was removed and the lipid pellets were washed with 100 μl of 20 mM HEPES (pH 7.4). The lipid pellets were solubilized in 1% Triton X-100 and the amount of radioactivity associated with the lipid pellets was measured. The amount of associated radioactivity reflects the amount of diffusion across the liposome membrane. The following results were obtained:

TABLE 1

| Permeability Enhancer | % Liposome Associated |
| --- | --- |
| $H_2N$—$(CH_2)_n$—COOH glycine n = 1 | 0.55 |
| Aminobutyric Acid n = 3 | 0.53 |
| Aminocaproic Acid n = 5 | 0.70 |
| Aminocaprylic Acid n = 7 | 9.54 |
| m-Aminobenzoic Acid ($H_2N$—$C_6H_4$—COOH) | 2.54 |
| Urocanic Acid | 0.95 |

The purpose of the liposomes was to serve as a cell membrane in the absence of metabolism. The aminocaprylic acid enhancer showed the highest degree of membrane association. Membrane association is due to diffusion of the enhancer:polymer complex across the liposome membrane. The liposomes were treated with micrococcal nuclease sufficient to digest all the ribozyme within a 1 minute incubation at room temperature. Fifty percent of the ribozyme was released from the liposomes indicating that 50% was associated with the outside of the membrane.

A titration of the permeability enhancer to ribozyme was performed by holding the amount of ribozyme constant and increasing the molar charge ratio of the permeability enhancer (aminocaprylic acid) to ribozyme. The experiment was carried out as described above using different amounts of enhancer. The following results were obtained:

TABLE 2

| Molar Charge Ratio | % Liposome Associated |
| --- | --- |
| 0.5 | 1.58 |
| 1.0 | 1.42 |
| 2.5 | 1.50 |
| 5.0 | 1.84 |
| 10.0 | 2.30 |
| 20.0 | 3.05 |
| 50.0 | 12.06 |

These results show that as the ratio of aminocaprylic acid to ribozyme is increased there is a concomitant increase in membrane association.

Taken together, the results from these two sets of experiments show that a monomeric cation can increase the intrinsic hydrophobicity of a ribozyme to facilitate migration across a lipid membrane.

EXAMPLE 2

Diffusion Across Into HeLa Cells

This example illustrates the ability of an enhancer to facilitate the diffusion of a ribozyme into HeLa cells. Radiolabeled $^{32}$P-ribozyme was complexed with aminocaprylic acid at a ratio of 20 molecules per mole of ribozyme phosphate as described in Example 1, in 50 μl of water to give a pH of about 4. The sample was diluted up to 1 ml with DMEM media containing no serum and added to HeLa cells. A control was run containing $^{32}$P-ribozyme without enhancer. Cells were incubated for 1 hour at 37° C. in 5% $CO_2$. The cells were washed 3 times with serum free media and solubilized with 0.5 ml of 1% triton. The amount of cell associated radioactivity was 3 fold higher with enhancer:ribozyme than with ribozyme alone indicating that the enhancer facilitated diffusion of the ribozyme into the HeLa cells.

Other embodiments are within the following claims.

I claim:

1. A method for enhancing permeability of a negatively charged polynucleotide, comprising the step of contacting said polynucleotide with a permeability enhancer molecule comprising a cationic group which carries between 0 and 10% of a positive charge at pH 7.4, and carries a greater than 50% positive charge at a pH between 5.0 and 6.0 covalently joined to an anionic group which is greater than 50% unprotonated at pH 7.4, and no greater than 10% unprotonated at pH 5.0 to 6.0, wherein said negatively charged polynucleotide is ion-paired to said cationic group.

2. A method for enhancing permeability of a negatively charged polynucleotide, comprising the step of contacting said polynucleotide with a permeability enhancer molecule comprising a cationic group which carries at least a 90% positive charge at both pH 7.4 and 5.0 covalently joined to an anionic group which is greater than 50% unprotonated at pH 7.4, and no greater than 10% unprotonated at pH 5.0 to 6.0, wherein said negatively charged polynucleotide is ion-paired to said cationic group.

3. The method of claim 1 or 2, wherein said enhancer molecule is provided in an amount of at least one enhancer molecule per negative charge on said polynucleotide.

4. The method of claim 1, wherein said contacting is at acidic pH so that said enhancer molecule has a net positive charge and ion-pairs with said polynucleotide.

5. The method of claim 2 or 4, wherein said polynucleotide is RNA or DNA and said enhancer molecule ion-pairs with the phosphate groups in said polynucleotide.

6. The method of claim 4 wherein formation of the ion-pair increases the intrinsic hydrophobicity of said polynucleotide allowing said polynucleotide to diffuse across a cell membrane.

7. The method of claim 6, wherein when said polynucleotide is present in a cytoplasm having a pH of about 7.4, said cationic group is deprotonated resulting in a negative charge, and said anionic group is deprotonated yielding no charge, wherein said enhancer molecule dissociates from said polynucleotide and remains in solution.

8. The method of claim 3, wherein when said polynucleotide is present in a cytoplasm having a pH of about 7.0, said cationic group is deprotonated resulting in a negative charge, and said anionic group is deprotonated yielding no charge, wherein said enhancer molecule dissociates from said polynucleotide and remains in solution.

9. The method of claim 1 or 2, wherein said permeability enhancer molecule is provided co-encapsulated within a liposome with said polynucleotide.

10. The method of claim 1, wherein said cationic group is an aminobenzyl group or an imidazole group having a $pK_a$ between 4.0 and 5.0.

11. The method of claim 1 or 2, wherein said anionic group is a carboxylate group having a $pK_a$ between 4.5 and 5.5.

12. The method of claim 1 or 2, wherein said enhancer molecule further comprises a linker between said cationic and anionic groups.

13. The method of claim 12, wherein said linker is a hydrocarbon chain or a simple or complex aromatic hydrocarbon.

14. The method of claim 2, wherein said enhancer molecule comprises a guanidinium group or an amine group.

15. The method of claims 1, 2, 10 or 14, wherein said enhancer molecule is a polynucleotide comprising at least two monomeric units.

16. A permeability ligand-enhancer molecule comprising a targeting ligand covalently linked to a cationic group through a biological labile bond, said cationic group having a positive charge at pH 7.4, wherein cleavage of said biological labile bond yields a chemical group having a $pK_a$ between 4.0 and 6.0 covalently linked to said cationic group.

17. The molecule of claim 16, wherein said ligand is selected from the group consisting of a monoclonal antibody or fragment thereof, a peptide, a protein, a carbohydrate and a vitamin.

18. The molecule of claim 16, wherein said biological labile bond is an ester bond, a carbamoyl bond or a peptide bond.

19. The molecule of claim 16, wherein said cationic group ion-pairs to a negatively charged polymer selected from the group consisting of a polyaminoacid and a polynucleotide.

20. The molecule of claim 16, wherein said cationic group ion-pairs to a negatively charged polynucleotide selected from the group consisting of RNA and DNA and protein.

21. The molecule of claim 20, wherein said RNA is enzymatic RNA.

22. The molecule of claim 16, wherein said cationic group is an amine group.

23. The molecule of claim 16 or 22, wherein said biological labile bond is covalently linked to said cationic group by a linker selected from the group consisting of a hydrocarbon chain comprising between 3 and 10 carbon atoms, a polyethoxy chain and an aromatic moiety.

24. A method for introducing a negatively charged polynucleotide into the cytoplasm of a cell, comprising the step of contacting said cell with said negatively charged polynucleotide ion-paired to an enhancer molecule, said enhancer molecule comprising a targeting ligand covalently linked to a cationic group through a biological labile bond, said cationic group having a positive charge at pH 7.4, wherein cleavage of said biological labile bond yields a chemical group having a $pK_a$ between 4.0 and 6.0 covalently linked to said cationic group, wherein said negatively charged polynucleotide enters into said cytoplasm.

25. The method of claim 24, wherein said ligand is selected from the group consisting of a monoclonal antibody or fragment thereof, a peptide, a protein, a carbohydrate and a vitamin.

26. The method of claim 24, wherein said biological labile bond is an ester bond, a carbamoyl bond or a peptide bond.

27. The method of claim 24, wherein said negatively charged polynucleotide is selected from the group consisting of RNA and DNA.

28. The method of claim 27, wherein said RNA is enzymatic RNA.

29. The method of claim 24, wherein said cationic group is a terminal amine group.

30. The method of claim 24 or 29, wherein said biological labile bond is covalently linked to said cationic group by a linker selected from the group consisting of a hydrocarbon chain comprising between 3 and 10 carbon atoms, a polyethoxy chain and an aromatic moiety.

* * * * *